United States Patent [19]

Clark et al.

[11] Patent Number: 4,899,016

[45] Date of Patent: Feb. 6, 1990

[54] PURIFICATION PROCESS FOR ORGANIC FEEDSTOCKS

[75] Inventors: Keith R. Clark; Philip Richman, both of Houston, Tex.

[73] Assignee: UOP, Des Plaines, Ill.

[21] Appl. No.: 155,125

[22] Filed: Feb. 11, 1988

[51] Int. Cl.$^4$ .......................... C07C 7/12; C10G 17/00
[52] U.S. Cl. .................................. 585/826; 208/310 Z; 208/208 R; 585/820; 585/822
[58] Field of Search ....................... 208/310 Z, 208 R; 585/820, 822, 826

[56] References Cited

U.S. PATENT DOCUMENTS

| | | | |
|---|---|---|---|
| 3,274,099 | 9/1966 | Broughton | 585/826 |
| 3,360,582 | 12/1967 | Mattox | 585/820 |
| 3,654,144 | 4/1972 | Collins | 208/245 |
| 4,433,195 | 2/1984 | Kulprathipanja | 585/820 |
| 4,795,545 | 1/1989 | Scmidt | 208/310 Z |

FOREIGN PATENT DOCUMENTS 0004619 10/1979 European Pat. Off.
0827532 8/1981 U.S.S.R.
1510705 5/1978 United Kingdom .

Primary Examiner—Patrick P. Garvin
Assistant Examiner—E. D. Irzinski
Attorney, Agent, or Firm—Thomas K. McBride

[57] ABSTRACT

Organic feedstocks containing at least one impurity component which is more strongly adsorbed on molecular sieve adsorbents than the host feedstock are purified of the said impurity by passage in the liquid phase through a fixed bed of the adsorbent whereby the impurity is selectively adsorbed and the purified feedstock recovered in unusually high yield by a novel bed regeneration procedure involving the use of a portion of the purified feedstock in the vapor phase to countercurrently remove the liquid held in the bed void space, a relatively non-sorbable purge gas to sequentially displace the purified feedstock vapor from the bed followed by a displacement of the non-sorbable purge gas from the bed void space using another portion of the purified feedstock in the vapor phase, and finally cooling and refilling the bed in a direction cocurrent with the flow of feedstock into the bed during the adsorption purification stage with a portion of the purified feedstock in the liquid phase.

6 Claims, 1 Drawing Sheet

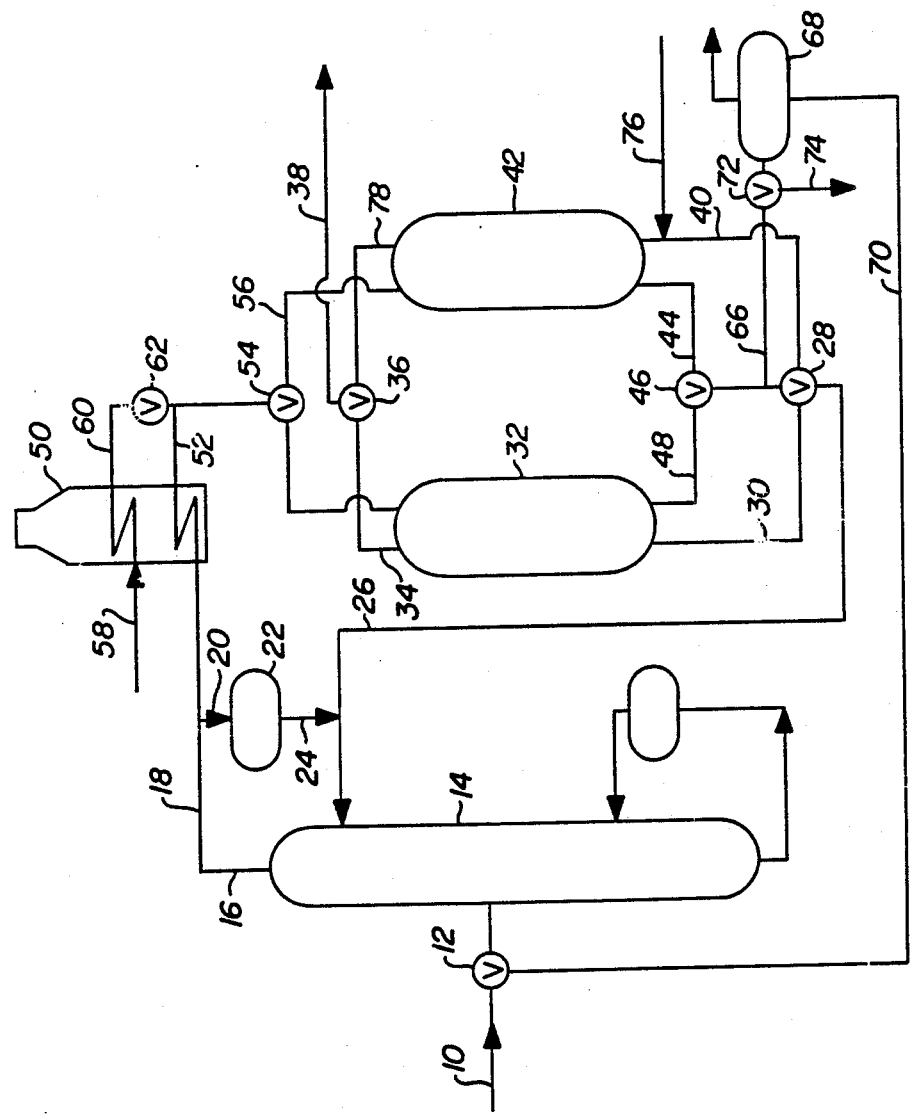

PURIFICATION PROCESS FOR ORGANIC FEEDSTOCKS

FIELD OF THE INVENTION

The present invention relates in general to the purification of organic feedstocks and more particularly to the purification of such feedstocks which contain at least one impurity component more strongly adsorbed on a molecular sieve adsorbent than the purified feed. The process is advantageously employed where it is desired to reduce the loss of purified product caused by coadsorption and "sponging" on the adsorbent. The process, which is carried out in the liquid phase during the adsorption purification step, makes use of vapor phase purified product or feedstock as well as a non-sorbable purge gas during adsorbent bed regeneration.

DESCRIPTION OF THE PRIOR ART

The purification in the liquid phase of organic feedstocks such as hydrocarbons containing sulfur compound impurities by the selective adsorption of the impurity compounds on molecular sieve adsorbents is well known in the art. For example, the liquid phase purification of petroleum-derived full range hydrocarbon feedstocks containing carbonyl sulfide is disclosed in U.S. Pat. No. 3,654,144 issued to J. J. Collins, Apr. 4, 1972, Therein the process comprises passing the sour hydrocarbon feed in the liquid phase through a fixed bed of a bivalent metal cation form of zeolite A to selectively adsorb the COS. The periodic regeneration of the adsorbent bed is accomplished in the vapor phase using a non sorbable purge gas such as nitrogen for displacement of the void space liquid as well as desorption of the COS impurity. This procedure is typical of the prior art processes insofar as regeneration is concerned. The entire volume of the gas stream used for displacement and purge desorption is isolated from the system and is largely a waste material. Equally disadvantageous economically, is the fact that the full bed void space volume of vapor phase hydrocarbon remaining in the bed along with a significant quantity of "sponged" liquid hydrocarbon and any coadsorbent hydrocarbon becomes admixed with the purge gas and/or the desorbed impurity constituent and is either not recovered as product or must be reclaimed by a further purification procedure.

SUMMARY OF THE INVENTION

There has now been discovered a novel process for purifying organic materials in which the impurity to be removed is more strongly adsorbed on a molecular sieve adsorbent than the non-impurity constituents, which permits the recovery as purified product of an appreciably greater proportion of the feedstock being treated. The process comprises the steps of:

(a) passing the impure organic feedstock in the liquid phase through a fixed bed containing a molecular sieve adsorbent capable of selectively adsorbing the impurity constituent to be removed, and terminating such passage prior to the time of breakthrough of an undesirable concentration of the impurity constituent;

(b) draining the bed of its void space held liquid, optionally with the assistance of a vapor phase stream of one or more of the constituents of the purified product in an amount and under temperature and pressure conditions such that substantially all of the adsorbed impurity remains adsorbed on the molecular sieve;

(c) countercurrently to the direction of flow into the bed in step (a), introducing a substantially non-sorbable purge gas into the bed at a rate which displaces the void space vapor from the bed without significant intermixing of the two gas phases and without desorbing the adsorbed impurity, and collecting the displaced vapor as product;

(d) continuing the flow of the non-sorbable purge gas through the bed, preferably at an elevated temperature, to desorb the adsorbed impurity and flush same from the bed and out of the adsorption-purification system;

(e) displacing the non-sorbable purge gas remaining in the bed at the termination of step (d) by the cocurrent flow, with respect to the direction of flow in step (d), thereinto of one or more constituents of the purified product of step (a) in the vapor phase; and (f) countercurrently with respect to the direction of flow in step (e) displacing the void space vapor remaining in the bed in step (e) by introducing in the liquid phase a portion of the purified product from step (a) in an amount sufficient to fill the bed void space and optionally cool the bed to the desired temperature for introducing additional impure feedstock to begin a new purification and regeneration cycle.

DETAILED DESCRIPTION OF THE INVENTION

As will readily be apparent to those skilled in the art, the enhanced recovery of purified product attributable to the present process is due in large part to the use of purified product, or one or more fractions thereof if the purified product is a mixture of two or more organic species, in the vapor phase to perform the displacement functions conventionally performed using a non-sorbable purge gas which is extraneous to the feedstocks being treated. During the bed draining and liquid displacement steps at the beginning of bed regeneration, the bed effluent is at no time contaminated with any materials not acceptable as a part of the purified product, thus greatly simplifying subsequent purification on recycle. At the end of the liquid displacement step the bed void space contains either purified product vapor or one or more constituents thereof which is supplemented by any constituents of the purified product which are coadsorbed with the impurity constituent during the initial adsorption purification step. Had an extraneous displacement gas been used in the draining and liquid displacement steps, the desorbed constituents of the purified product would be effectively lost as product by virtue of admixture with a non-product material. The use of the extraneous purge material is limited to plug flow displacement of product compatible material, which can be collected as product, and desorbing the impurity constituent of the feedstock to regenerate the adsorption capacity of the bed. As used herein, the term "plug flow" is intended to have its usual meaning in the art that displaced and displacing fluids in the bed are maintained with only a minimal intermixture at their interface in the bed. In addition to significantly increasing the purified product yield, the amount of extraneous purge gas required is also reduced, usually to economic advantage.

The molecular sieve adsorbent used in the process is not a narrowly critical aspect of the invention and is selected with regard to the molecular dimensions, polarity, volatility and the like of the impurity constituent to be removed. Zeolitic molecular sieves such as 13X, 4A and 5A widely used for adsorption-purification processes are preferred adsorbents. Non-zeolitic adsorbents such as the AlPO$_4$'s, SAPO's and MeAPO's more recently discovered and made available commercially are also suitably employed. Such materials are described in detail in the patent literature, for instance, U.S. Pat. Nos. 4,567,029, 4,310,440 and 4,440,871.

The organic feedstocks are also not a narrowly critical factor. Most commonly the hydrocarbon feedstocks derived from the various petroleum refining operations require adsorption purification since sulfur compounds are almost universal contaminants of the petroleum crudes and must be removed somewhere along the processing chain to avoid atmospheric contamination when the final products are burned as fuel. The process is especially useful in the removal of COS from propane, but other feedstocks such as ethane, butane, natural gasoline, propylene, butylene, $C_2$ through $C_4$ paraffins, olefins and diolefins generally are suitably treated. The major requirements of the feedstocks are (a) that they can exist in both the liquid and the vapor phase under the temperature and pressure conditions which can reasonably be imposed on the adsorption system, and (b) that the impurity to be removed is more strongly adsorbed on the adsorbent under the imposed treatment conditions than the purified product constituents.

The temperature and pressure conditions, flow rates, adsorption bed sizes and configurations will vary depending upon the feedstock being treated but their selection is well within the routine skill of the art.

THE DRAWINGS

The sole FIGURE of the drawings is a schematic flow diagram of one embodiment of the present process.

ILLUSTRATATIVE EMBODIMENT

The various embodiments of the present invention are illustrated by the following specific process system which concerns the removal of carbonyl sulfide from propane. The source of the propane is a natural gas stream which has been treated in a depropanizer column and a deethanizer column to remove ethane and propane. In this embodiment, the overhead from the dethanizer column (hereinafter "DEO") is conveniently employed as the extraneous non sorbable purge gas.

With reference to the figure of the drawing, the bottoms effluent from a natural gas deethanizer column is fed through line 10 and valve 12 to depropanizer column 14. The overhead from column 14 which comprises propane and COS, as an impurity constituent, passes through lines 16, 18, and 20, condenser 22, line 24 and 26, valve 28 and line 30 into the bottom of adsorbent bed 32 which contains zeolite 5A. Bed 32 has, at the beginning of the adsorption purification step, been regenerated, cooled to 90° F. and filled with feedstock. The flow rate of feedstock into bed 32 through line 30 is from about 56,000 to 66,000 pounds per hour. Purified propane is recovered through line 34, valve 36 and line 38, while COS is retained in bed 32 as an adsorbate. The bed capacity is such that the adsorption-purification step proceeds for 8.0 hours, after which time feedstock flow is diverted via valve 28 through line 40 and into adsorbent bed 42. During the 8 hour period, bed 32 is engaged in adsorption-purification, adsorbent bed 42 is undergoing regeneration following a similar adsorption-purification step therein. As the first stage of bed regeneration, the void space liquid is drained through line 44, valve 46 and line 48 and passed as a portion of the feedstock to bed 32. Draining and displacement of the liquid from bed 42 is aided by the introduction of overhead from depropanizer 14 which has been converted from liquid phase to the vapor phase by heating in furnace 50. The depropanizer overhead contains COS, but in terms of absolute quantities the vapor phase stream entering bed 42 from furnace 50 through line 52, valve 54 and line 56 imparts very little COS to the adsorbent of bed 42. At the beginning of the draining step, the temperature of the vapor stream entering bed 42 is initially about 150° F. and flows at the rate of 13,600 pounds per hour at 325 psig for a period of 0.5 hours. Over this period the temperature of the vapor stream is increased to 250° F. which aids in desorbing coadsorbed propane from the adsorbent mass without appreciably desorbing COS impurity. Thereafter, over the period of the next 15 minutes, the vapor phase propane in the bed void space is displaced by the plug flow introduction of the vapor phase overhead from the deethanizer (DEO) through line 58 to furnace 50, wherein the gas is heated to about 150° F., line 60 valve 62 and 54, and line 56. The DEO is stream is at a pressure of 400 psig and flows at the rate of 33,000 pound per hour. The propane vapor leaving bed 42 is fed through line 44, valve 46, line 66 and valve 72 to condenser 68 and then recycled to the depropanizer column 14 through line 70 and valve 12. The flow of DEO into bid 42, is continued for an additional 1.25 hours, optionally with increasing temperature of the DEO up to about 550° F. It is possible during this period to recover additional propane by recycling the bed effluent to the deethanizer unit, or the effluent can be vented from the system. In the next stage of the regeneration the adsorbed COS is desorbed b the continued floe of DEO at 550° F. and at the same flow rate and pressure as used to displace the void space propane vapor. The desorbed COS and DEO purge gas is vented from the system through valve 72 and line 74. The COS desorption period is 4.0 hours and at the end of that period the flow of DEO is terminated and the DEO in the bed void space is displaced using the propane vapor stream from depropanizer column 14 through lines 16 and 18, furnace 50, line 52, valve 54 and line 56, at a flow rate of 13,600 pounds per hour, a temperature of 150° F. to 250° F. and a pressure of 335 psig. The DEO vapor is passed from bed 42 through line 44, valve 46, line 66, valve 72 and line 74. This displacement stage requires 15 minutes. As the final stage of regeneration, bed 42 is refilled with liquid phase product propane introduced into the bed 42 via line 76 at the rate of 56,000 pounds per hour at 300 psig and at a temperature of 90° F. As the bed is filled with purified propane and cooled the propane vapor in the void space is either recycled to the depropanizer column 14 (conduits not shown) or recovered as product.

What is claimed is:

1. Process for purifying an organic feedstock which comprises the steps of:
    (a) passing the impure organic feedstock in the liquid phase through a fixed bed containing a molecular sieve adsorbent capable of selectively absorbing the impurity constituent to be removed, and terminating such passage prior to the time of breakthrough of an undesirable concentration of the impurity constituent;

(b) draining the bed of its void space held liquid, by displacing said liquid with vapor containing constituents of the purified product;
(c) countercurrently to the direction of flow into the bed in step (a), introducing a substantially non-sorbable purge gas into the bed at a rate which displaces the void space vapor from the bed without significant intermixing of the two gas phases and without desorbing the adsorbed impurity and collecting the displaced vapor as product;
(d) continuing the flow of the non-sorbable purge gas through the bed to desorb the adsorbed impurity and flush same from the bed and out of the adsorption-purification system;
(e) displacing the non-sorbable purge gas remaining in the bed at the termination of step (d) by the cocurrent flow, with respect to the direction of flow in step (d), thereinto of vapor phase stream comprising one or more constituents of the purified product of step (a); and
(f) countercurrently with respect to the direction of flow in step (e) displacing the void space vapor remaining in the bed in step (e) by introducing in the liquid phase a portion of the purified product from step (a) in an amount sufficient to fill the bed void space and cool the bed to the desired temperature for introducing additional impure feedstock to begin a new purification and regeneration cycle.

2. Process according to claim 1 wherein the organic feedstock is a hydrocarbon containing from 3 to 6 carbon atoms.

3. Process according to claim 2 wherein the hydrocarbon is propane and the impurity to be removed in a sulfur compound.

4. Process according to claim 3 whereas the sulfur compound is carbonyl sulfide.

5. Process according to claim 1 wherein in step (b) the draining of the bed is accomplished with the assistance of the introduction into the bed of a vapor phase stream comprising one or more of the constituents of the purified product of step (a) in an amount and under temperature and pressure conditions such that substantially all of the adsorbed impurity remains adsorbed in the molecular sieve.

6. Process according to claim 1 wherein the molecular sieve adsorbent is a crystalline zeolite molecular sieve.

* * * * *